United States Patent [19]

Krenitsky et al.

[11] Patent Number: 5,539,098
[45] Date of Patent: Jul. 23, 1996

[54] 5'-O-PROPIONYL AND 5'-O-BUTYRYL ESTERS OF 2-AMINO-6-METHOXY-9-(β-D-ARABINOFURANOSYL)-9H-PURINE

[75] Inventors: Thomas A. Krenitsky, Chapel Hill; David J. T. Porter, Raleigh, both of N.C.

[73] Assignee: Glaxo Wellcome Inc., Research Triangle Park, N.C.

[21] Appl. No.: 403,363

[22] Filed: Mar. 14, 1995

Related U.S. Application Data

[63] Continuation of Ser. No. 110,487, Aug. 23, 1993, which is a continuation of Ser. No. 725,865, Jul. 3, 1991, Pat. No. 5,424,295, which is a continuation of Ser. No. 444,178, Nov. 30, 1989, abandoned, which is a continuation-in-part of Ser. No. 200,022, May 27, 1988, abandoned.

[30] Foreign Application Priority Data

May 30, 1987 [GB] United Kingdom ............... 8712745

[51] Int. Cl.$^6$ ........................... C07H 19/19; A61K 31/70
[52] U.S. Cl. ............................................. 536/27.81
[58] Field of Search ........................ 514/45; 536/27.81

[56] References Cited

U.S. PATENT DOCUMENTS 5,424,295 6/1995 Krenitsky et al. ...................... 514/45

*Primary Examiner*—Gary L. Kunz
*Attorney, Agent, or Firm*—George W. Neuner

[57] ABSTRACT

The 5'-O-proprionyl and 5'-O-butyryl esters of 2-amino-6-methoxy-9-(B-D-arabinofuranosyl)-9H-purine useful as inhibitors of varicella zoster virus.

2 Claims, No Drawings

5'-O-PROPIONYL AND 5'-O-BUTYRYL ESTERS OF 2-AMINO-6-METHOXY-9-(β-D-ARABINOFURANOSYL)-9H-PURINE

This is a continuation of application(s) Ser. No. 08/110,487 filed Aug. 23, 1993 which is a continuation of 07/725,865, filed Jul. 3, 1991, now U.S. Pat. No. 5,424,295, which is a continuation of Ser. No. 07/444,178, filed Nov. 30, 1989 now abandoned which is a continuation in part of Ser. No. 07/200,022, filed May 27, 1988 now abandoned.

FIELD OF THE INVENTION

The present invention relates to certain substituted purine arabinosides and physiologically acceptable derivatives thereof, in particular esters, and their use in the treatment of varicella zoster virus infections.

BACKGROUND OF THE INVENTION

Varicella zoster virus (VZV) which causes chicken-pox and shingles, is a DNA virus of the herpes family. Varicella (chicken-pox) is the primary disease produced by VZV in a host without immunity; it is usually a mild illness of young children which is manifested as fever and an itching rash. Herpes zoster (shingles) is the recurrent form of the disease occurring in adults who were previously infected with the varicella-zoster virus. The clinical manifestations of this infection are characterized by neuralgia and a vesicular skin rash that is unilateral and dermatomal in distribution. Spread of inflammation may lead to paralysis or convulsions, and coma if the meninges become affected.

SUMMARY OF THE INVENTION

It has now been found that certain purine arabinonucleosides described below characterized by the presence of groups substituted at the 2- and 6-positions of the purine ring have potent activity against human virus infections caused by varicella zoster virus (VZV) and thus are useful in treating such infections including shingles in humans.

Purine arabinonucleosides including 9-β-D-(arabinofuranosyl)-6-methoxy-9 H-purine, 9-(β-D-arabinofuranosyl)-6-pyrrolidino-9 H-purine, 9-(β-D-arabinofuranosyl)-6-methylamino-9 H-purine and 9-(β-D-arabinofuranosyl)-6-dimethylamino-9 H-purine have previously been described in J. Org. Chem. 27, 3274–9 (1962); Cancer Treatment Rep. 60(10), 1567–84, (1976); Tetrahedron 40(4), 709–13, (1984); Canada J. Biochem. 4 43(1), 1–15 (1965); J. Med. Chem. 12, 498–504, (1969); J. Biol. Chem. 251(13), 4055–61 (1976); Ann. N.Y. Acad. Sci. 284, 81–90 (1977); EP002192; U.S. Pat. No. 3,666,856; U.S. Pat. No. 4,371,613; U.S. Pat. No. 3,758,684; U.S. Pat. No. 4,055,718; U.S. Pat. No. 4,048,432; U.S. Pat. No. 4,055,717.

DETAILED DESCRIPTION OF THE INVENTION

Thus in the first aspect of the present invention there is provided a compound of formula (I):

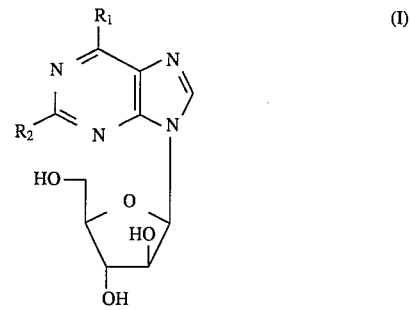

wherein $R_1$ represents a halogen (e.g., chlorine or iodine) atom, a $C_{1-5}$ alkoxy group (e.g., methoxy or ethoxy); halogen-substituted $C_{1-5}$ alkoxy (e.g., trifluoroethoxy); an amino group which is mono- or di-substituted by $C_{1-5}$ alkyl (e.g., methyl or ethyl), $C_{1-5}$ alkyl substituted by one or more fluorine atoms (e.g., 2-fluoroethyl or 2,2,2-trifluoroethyl), or $C_{3-6}$ cycloalkyl (e.g., cyclopropyl), or the amino member of a ring containing 4–7 carbon atoms and optionally a double bond (e.g., pyrrolidino) and/or a further nitrogen atom; and $R_2$ represents hydrogen, halogen or amino provided that $R_1$ is not methoxy or dimethylamino when $R_2$ is H; and pharmaceutically acceptable derivatives thereof for the treatment of human vital infections caused by VZV.

The present invention also includes the compounds of formula (I) wherein $R_2$ is hydrogen and $R_1$ is piperidino or pyrrolidino and wherein $R_2$ is amino and $R_1$ is chlorine and the pharmaceutically acceptable derivatives thereof for use in treating VZV infections in humans.

In the above formula (I) the alkyl groups (including those in the alkoxy, alkylamino or dialkylamino groupings) are preferably methyl, ethyl or propyl groups.

Preferred compounds of formula (I) include those wherein:
(a) $R_2$ is hydrogen; and
(b) $R_1$ is $C_{2-5}$ alkoxy; or
(c) $R_1$ is $C_{2-5}$ alkylamino; or
(d) $R_1$ is halogen, e.g., iodo.

The following compounds are preferred compounds of the present invention by virtue of their potent antiviral activity against VZV;
1) 9-(β-D-Arabinofuranosyl)-6-methylamino-9 H-purine,
2) 9-β-D-Arabinofuranosyl)-6-ethoxy-9 H-purine,
3) 9-(β-D-Arabinofuranosyl)-6-iodo-9 H-purine,
4) 9-(β-D-Arabinofuranosyl)-2-amino-6-iodo-9 H-purine,
5) 9-(β-D-Arabinofuranosyl)-6-pyrrolidino-9 H-purine,
6) 9-(β-D-Arabinofuranosyl)-2-chloro-6-methylamino-9 H-purine,
7) 9-(β-D-Arabinofuranosyl)-6-cyclopropylamino-9 H-purine,
8) 9-(β-D-Arabinofuranosyl)-6-ethyl(methyl)amino-9 H-purine,
9) 9-(β-D-Arabinofuranosyl)-2-amino-6-methoxy-9 H-purine, and
10) 9-(β-D-Arabinofuranosyl)-6-n-propoxy-9 H-purine.

Of the above numbered compounds, compounds 1), 2), 3), 4) and 9) are especially preferred. The present invention also includes the novel compounds 2), 3), 4), 6), 7), 8), 9) and 10) listed above.

In a second aspect of the present invention there are provided the novel compounds of general formula I(a)

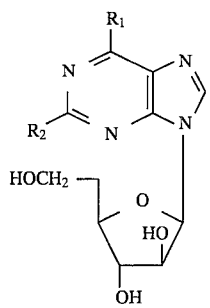

I(a)

wherein $R_1$ represents a halogen (e.g. chlorine or iodine) atom, a $C_{1-5}$ alkoxy group (e.g. methoxy or ethoxy); halogen-substituted $C_{1-5}$ alkoxy (e.g. trifluoroethoxy) an amino group which is mono- or di-substituted by $C_{1-5}$ alkyl (e.g. methyl or ethyl), $C_{1-5}$ alkyl substituted by one or more fluorine atoms (e.g. 2-fluoroethyl or 2,2,2-trifluoroethyl), or $C_{3-6}$ cycloalkyl (e.g. cyclopropyl) or the amino member of a ring containing 4–7 carbon atoms and optionally a double bond (e.g. pyrrolidino) and/or a further nitrogen atom; and $R_2$ represents hydrogen, halogen or amino provided that when $R_2$ is hydrogen, $R_1$ does not represent chlorine, methoxy, methylamino, ethylamino, dimethylamino, piperidino or pyrrolidino and when $R_2$ is amino, $R_1$ does not represent chlorine or methylamino; and pharmaceutically acceptable derivatives thereof other than the 2',3',5'-triacetate and -tribenzyl derivatives of the compounds of formula I(a) in which $R_1$ is chlorine or fluorine when $R_2$ is chlorine, fluorine, hydrogen or amino.

The present invention further includes a compound of formula I(a) for use in the treatment of human viral infections caused by VZV.

In a further aspect of the present invention there are provided pharmaceutically acceptable derivatives of the compounds of formula (I) namely any pharmaceutically acceptable ether, ester or salt of such ester, or any other compound which, upon administration to a human subject is capable of providing (generating) a compound of formula (I) or an antivirally active metabolite thereof in said human as a result of human and/or viral enzymes. Thus the pharmaceutically acceptable derivatives described herein are useful in the treatment of VZV infections in humans.

The pharmaceutically acceptable esters of the above compounds of formula (I) are particularly preferred since they are capable of providing high levels of the parent compound of formula (I) or (Ia) in the plasma of a subject after oral administration. The present invention particularly provides as a preferred class of novel compounds the pharmaceutically acceptable esters formed by esterification of the 2'-, 3'- and/or 5'-hydroxy group of the arabino-sugar moiety.

Other preferred derivatives of compounds of formula (I) include mono- di- or tri-esters of the arabino-sugar residue substituted at the 2'-, 3'- and 5'-positions of said residue.

Such preferred esters include carboxylic acid esters in which the non-carbonyl moiety of the ester grouping is selected from straight or branched chain alkyl (e.g. n-propyl, t-butyl, n-butyl), alkoxyalkyl (e.g. methoxymethyl), aralkyl (e.g. benzyl), aryloxyalkyl (e.g. phenoxymethyl), aryl (e.g. phenyl) optionally substituted by halogen, $C_{1-4}$ alkyl or $C_{1-4}$ alkoxy, nitro or amino; sulphonate esters such as alkylsulphonyl; or alkylarylsulphonyl (e.g. methanesulphonyl or tosylsulphonyl); amino acid esters such as aliphatic and aromatic (e.g. aryl) amino acid esters (e.g. Gly, Ala, Leu, lie, Phe, Tyr and Trp) and other natural occurring amino acid esters as well as esters of β-alanine; and mono-, di- or triphosphate esters. Pharmaceutically acceptable salts of these esters include sodium, potassium, $NR_4^+$ where R=H or $C_{1-6}$ alkyl when the esters contain acidic groups, and acid addition salts when the esters contain basic (e.g., amino) groups. In the above ester groups, the alkyl groups (including those in alkoxy groupings) contain 1 to 12 carbon atoms preferably 1 to 4 carbon atoms and the aryl groups are preferably phenyl.

The purine nucleosides of formula (I) and their derivatives will be hereinafter referred to as compounds according to the invention or as active ingredients.

In a further, preferred aspect of the present invention, there is provided the use of a compound according to the invention in the manufacture of a medicament for the treatment of human viral infections caused by VZV.

The present invention further provides a method for the treatment of VZV infections in a human subject which comprises administering to the said human subject an effective amount of a compound according to the invention.

The method hereinbefore described includes inhibiting the replication of VZV viruses in host cells of a mammal which comprises applying an effective virus replication inhibiting amount of the compound of formula (I), or a pharmaceutically acceptable derivative thereof, to the infected cells.

Examples of the clinical conditions caused by VZV infections which may be treated in accordance with the invention include those referred to above.

The compound of formula (I) and pharmaceutically acceptable derivatives thereof (hereafter collectively referred to as the active ingredients) may be administered by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient.

For each of the above-indicated utilities and indications the amount required of an active ingredient (as above defined) will depend upon a number of factors including the severity of the condition to be treated and the identity of the recipient and will ultimately be at the discretion of the attendant physician. In general, however, for each of these utilities and indications, a suitable, effective dose will be in the range 0.1 to 250 mg per kilogram body weight of recipient per day, preferably in the range 0.1 to 100 mg per kilogram body weight per day and most preferably in the range 1 to 20 mg per kilogram bodyweight per day; an optimum dose is about 10 mg per kilogram body weight per day (unless otherwise indicated all weights of active ingredient are calculated as the parent compound of formula (I); for salts and esters thereof the figures would be increased proportionately). The desired dose is preferably presented as two, three, four or more sub-doses administered at appropriate intervals throughout the day. These sub-doses may be administered in unit dosage forms, for example, containing 5 to 1000 mg, preferably 20 to 500 mg and most preferably 100 to 400 mg of active ingredient per unit dosage form.

While it is possible for the active ingredients to be administered alone it is preferable to present them as pharmaceutical formulations. The formulations of the present invention comprise at least one active ingredient, as above defined, together with one or more acceptable carriers thereof and optionally other therapeutic ingredients. The carrier(s) must be "acceptable" in the sense of being compatible with the other ingredients of the formulation and not deleterious to the recipients thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compression tablets may be prepared by compressing in an suitable machine the active ingredient in a free-flowing form such as a powder or granules, optionally mixed with a binder (e.g. povidone, gelatin, hydroxypropylmethylcellulose), lubricant, inert diluent, preservative, disintegrant (e.g. sodium starch glycollate, cross-linked povidone, cross-linked sodium carboxymethyl cellulose), surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide the desired release profile.

For infections of the eye or other external tissues, e.g., mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream may include, for example, at least 30% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with an lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a pardde size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as; for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The phosphate esters of this invention may be encapsulated in liposomes using methods well known in the art. The liposome formulations of these phosphate esters, preferably the monophosphates, most preferably the 5'-monophosphates, are included within the scope of this invention.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention also provides a process for the preparation of a compound of formula I(a), or a pharmaceutically acceptable derivative, especially an ester, thereof comprising either:

A. reacting a compound of formula (II)

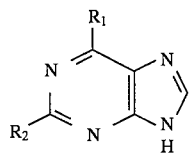

wherein $R_1$ and $R_2$ are as hereinbefore defined, with a compound of formula (III)

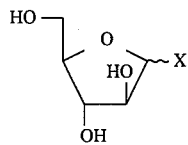

wherein X represents a pyrimidine or purine base (other than a compound of formula (II)); or B. reacting a compound of formula (IV)

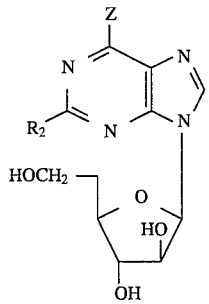

wherein Z is a leaving group and $R_2$ is as hereinbefore defined, with a compound capable of introducing the necessary group at the 6-position; and optionally thereafter or simultaneously therewith, where the resulting compound is a compound of formula (I), converting it into a pharmaceutically acceptable derivative thereof Or where the resulting compound is a pharmaceutically acceptable derivative converting it into a different pharmaceutically acceptable derivative or a compound of formula (I).

With regard to process A), X is advantageously a uracil base. The reaction may be effected, for example, by treatment of the compounds of formulae (II) and (III) with an enzyme such as a phosphorylase enzyme, for example, a mixture of uridine phosphorylase and purine nucleoside phosphorylase in the presence of inorganic phosphate at an pH of 5.0–9.0 and a temperature of 15°–90° C. advantageously 40°–60° C.

Regarding process B) this this may be carried out in accordance with the procedure described by Reist. E. J. et al., *J. Org. Chem.* 27 (1962) 3274–3279. A convenient leaving group is a halogen atom for example chlorine, the reaction being advantageously carried out in an organic solvent, e.g., absolute methanol, with an agent capable of providing the necessary group at the 6-position for example, an appropriate amine in the case where $R_1$ represents an alkyl- or dialkylamino group.

Physiologically acceptable esters and salts of the compounds of formula (I) may be prepared in conventional manner for example esters may be prepared by esterification of the parent compound with an appropriate acyl halide or anhydride. Alternatively the esters may be prepared by displacing an appropriate leaving group, e.g., halide, with an appropriate carboxylic acid or by opening an appropriate anhydro nucleoside of the parent compound with an appropriate carboxylic acid or salt thereof.

The following Examples illustrate the present invention but should not be considered in anyway limiting of the invention.

EXAMPLE 1:
9-β-D-Arabinofuranosyl-6-methylamino-9 H-purine

6-Thiol-9-(β-D-arabinofuranosyl)-9 H-purine (Reist E. J. et al., *J. Org. Chem.* 27 (1962) 3274–3279) (0.35 mmole, 100 mg) and 5 ml of absolute methanol were combined and cooled to –10° C. while protected from moisture. Chlorine gas was bubbled gently through the suspension for 2 min. The resulting solution was stirred for 5 min at –10° C. then dry nitrogen was bubbled through the cold solution for 15 min until the excess chlorine was removed. Two milliliters of 40% aqueous methylamine was added to the reaction mixture, which was then heated in a stainless steel bomb at 115° C. for 4.5 hr. The bomb was cooled to 0° C. and the contents were evaporated to dryness, providing an 88% yield of the title compound. After recrystallization in water the sample had a melting point of 201.5°–202.5° C.

EXAMPLE 2: 9-β-D-Arabinofuranosyl-6-ethoxy-9 H-purine

6-Ethoxypurine (Sigma Chemical Co. St. Louis, Mo.) (3.05 mmoles, 0.5 g) and uracil arabinoside (6.09 mmoles, 1.48 g) were suspended in 100 ml of a 10 mM potassium phosphate, 0.04% potassium azide solution with a pH of 7.4. Purified uridine phosphorylase (6000 I.U.) and purine nucleoside phosphorylase (8400 I.U.) (Krenitsky, T. A., et al. *Biochemistry*, 20, 3615 (1981) and U.S. Pat. No. 4,381,344) were added and the suspension stirred at 35° C.

After 168 hours an additional 18000 units of uridine phosphorylase and 75600 units of purine nucleoside phosphorylase were added. Seven days later the reaction was filtered and the flitrate chromatographed on a column containing Dowex-I-hydroxide resin (2.5×8 cm). The column was eluted with 90% methanol/water (v/v) and fractions containing product were combined and the solvent removed under vacuum. The residue was dissolved in 30% n-propanol and water (v/v) and chromatographed on a column containing BioRad P-2 (5×90 cm). The product was eluted with 30% n-propanol/water (v/v). Product-containing fractions were combined and the solvent removed under vacuum, yielding 0.363 g of 9-β-D-arabinofuranosyl-6-ethoxy-9 H-purine that analyzed as a 0.3 hydrate. NMR and mass spectrometry were consistent with the structure.

Anal. Calcd. for $C_{12}H_{16}N_4O_5 \cdot 0.3H_2O$: Calcd: C, 47.78; H, 5.55; N, 18.57. Found: C, 47.99; H, 5.54; N, 18.40.

EXAMPLE 3: 9-β-D-Arabinofuranosyl-6-iodo-9 H-purine

6-Iodopurine (Sigma Chemical Co. St. Louis, Mo.) (4 mmoles, 1 g) was dissolved in 15 ml of 1,2-dimethoxyethane with heating. Fifty milliliters of a uracil arabinoside solution (10.1 mmoles)in 10 mM potassium phosphate, 0.04% potassium azide solution, pH of 7.4, were added. Purified uridine phosphorylase (6800 I.U.) and purine nucleoside phosphorylase (12000 I.U.) were added and the reaction stirred at 35° C. After 21 days an additional 4800 units of uridine phosphorylase and 20000 units of purine nucleoside phosphorylase were added, Ninety days later the reaction was filtered and the solvent removed under vacuum. The residue was suspended in 100 ml of water, heated with steam, and then filtered. The flitrate was chromatographed on a column containing XAD-2 resin (5×35 cm), eluting with 2 liters of water followed by 2 liters ethanol. Fractions containing product were combined-and the solvent removed under vacuum. The residue was dissolved in 30% n-propanol/water (v/v) and chromatographed on a column containing BioRad FP-2 (5×90 cm). The product was eluted with 30% n-propanol/water (v/v). Product-containing fractions were combined and the solvent removed under vacuum. The residue was dissolved in 30% n-propanol/water (v/v) and chromatographed on a Sephadex G-10 column (5×90 cm). This column was eluted with 30% n-propanol/water (v/v). Product-containing fractions were combined and after removing the solvent under vacuum, yielded 0.253 g of 9-β-D-arabinofuranosyl-6-iodo-9 H-purine that analyzed as a 1.5 hydrate. NMR and mass spectrometry were consistent with the structure.

Anal. Calcd. for $C_{10}H_{11}IN_4O_4 \cdot 1.5\ H_2O$: Calcd: C, 29.65; H, 3.48; N, 13.83; I, 31.32. Found: C, 29.43; H, 3.53; N, 13.66; I, 31.20.

EXAMPLE 4: 9-β-D-Arabinofuranosyl-2-amino-6-iodo-9 H-purine

2-Amino-6-iodopurine (Sigma Chemicals, St. Louis. Mo.) (25.5 mmoles, 6.75 g) and uracil arabinoside (61.9 mmoles. 15.1 g) were combined in 0.31 liters of 10 mM potassium phosphate pH 6.9 with 0.02% potassium azide. Purified purine nucleoside phosphorylase (17000 units) and uridine phosphorylase (2000 units) were added and the solution stirred at 37° C. After 18 days an additional 5700 units of uridine phosphorylase were added. Fifty-seven days later the reaction was filtered and the flitrate chromatographed on a column containing XAD-2 resin (8×11 cm). The product was eluted with a step gradient of ethanol/water (v/v) as follows: 0.35 liter 10%; 1 liter 20%; 1 liter 50%; 0.2 liter 95%. Product-containing fractions were combined and the ethanol removed under vacuum. The residue was dissolved in 30% n-propanol/water (v/v) and chromatographed on a 7.5×90 cm column containing BioRad P-2 resin, This procedure yielded 1.1 g of 9-β-D-arabinofuranosyl-2-amino-6-iodo-9 H-purine as a 0.5 hydrate. NMR and mass spectrometry were consistent with the structure.

Anal. Calcd. for $C_{10}H_{12}IN_5O_4 \cdot 0.5H_2O$: Calcd: C, 29.87; H, 3.26; N, 17.4. Found: C, 29.86; H, 3.29; N, 17.39.

EXAMPLE 5: 9-β-D-Arabinofuranosyl-6-pyrrolidino-9 H-purine

6-Pyrrolidinopurine (Sigma Chemical Co., St. Louis, Mo.) (2.6 mmoles), 0.5 g, and uracil arabinoside (5.29 mmoles, 1.29 g) were suspended in 100 ml of a 10 mM potassium phosphate 0.04% potassium azide solution with a pH of 7.4. Purified uridine phosphorylase (6000 I.U.) and purine nucleoside phosphorylase (8400 I.U.) (Krenitsky, T. A., et al. Biochemistry, 20, 3615 (1981) and U.S. Pat. No. 4,381,344) were added and the suspension stirred at 35° C. Twenty days later the reaction was filtered and the filtrate chromatographed on a column containing Dowex-I-hydroxide resin (2.5×8 cm). The product was eluted from the column with 90% methanol/water (v/v). Fractions containing product were combined and the solvent removed under vacuum. The residue was dissolved in 50 ml of 30% n-propanol and water (v/v) and chromatographed on a BioRad P-2 column (5×90 cm). The product was eluted with 30% n-propanol/water (v/v). Product-containing fractions were combined and the solvent was removed under vacuum yielding 0.573 g of 9-β-D-arabinofuranosyl-6-pyrrolidino-9 H-purine. NMR and mass spectrometry were consistent with the structure.

Anal. Calcd. for $C_{14}H_{19}N_5O_4$: Calcd: C, 52.33; H, 5.96N, 21.79. Found: C, 52.60; H, 6.09; N, 21.51.

EXAMPLE 6: 9-β-D-Arabinofuranosyl-2-chloro-6-methylamino-9 H-purine

A solution of 2,6-dichloro-2',3',5'-tri-O-benzyl-9-(β-D-arabinofuranosyl)purine (Keller, F. et al., J. Org. Chem., 32, 1644 (1967); Montgomery, J. A. and Hewson, K. J., J. Med. Chem. 12, 498 (1967)) (5.92 g, 10 mMoles) in benzene (35 ml of a solution of 0.6 g methylamine per 10 ml benzene) was kept at room temperature in a sealed bomb for 4 days. The bomb was cooled thoroughly in ice, opened, and the contents filtered to remove methylamine hydrochloride. The solvent was removed in vacuo to give an oil that was combined with an oil from a reaction of the same scale, but conducted at 125° C. The total weight was 11.4 g. TLC showed it was mixture of starting material, mono-and dimethylamino compounds. The oil was chromatographed on 285 g silica gel using 30% acetone and 70% cyclohexane by volume. The component running below starting material (TLC, silica gel, 3:7 acetone:cyclohexane) was collected and the solvent removed in vacuo. Yield: 4.8 g of 2-chloro-6-methylamino-2',3',5'-tri-O-benzyl-9-(β-D-arabinofuranosyl)purine, as an oil. A 1.1 g portion of this in 40 ml 2-methoxyethanol was added to palladium chloride (0.87 g) that was prereduced in a Parr apparatus. This was hydrogenated at 50 psi for 30 min with the hydrogen atmosphere changed after the initial 15 min. The catalyst was removed by filtration through a bed of Celite and washed with methanol. The filtrate was neutralized by the addition of Dowex-1 ($HCO_3$). The resin was removed by filtration and washed with methanol. The filtrate was evaporated in vacuo and the residue triturated with chloroform. The crude product was washed with hot water, dissolved in hot methanol, filtered, cooled, and the solid collected. Crystallization from boiling water gave the title compound as a hydrate. Yield 44.5 mg; mp 224°–225° C.

Anal. Calcd. for $C_{11}H_{14}N_5O_4Cl \cdot H_2O$: Calcd: C, 39.59; N, 20.99; H, 4.83. Found: C, 39.27; N, 20.83; H, 5.16.

EXAMPLE 7: 9-β-D-Arabinofuranosyl-6-cyclopropylamino-9 H-purine

6-Cyclopropylaminopurine (prepared by nucleophilic displacement of the chlorine group on 6-chloropurine (Sigma Chemicals, St. Louis Mo.) by cydopropylamine in acetonitrile) (2.85 mmoles, 0.5 g) and uracil arabinoside (Torrenee, P. F. et al. *J. Med. Chem.*, 22(3), 316–319 (1979)) (5.71 mmoles, 1.39 g) were suspended in 100 ml of a 10 mM potassium phosphate, 0.04% potassium azide solution with a pH of 7.4. Purified uridine phosphorylase (6000 I.U.) and purine nucleoside phosphorylase (8400 I.U.) (Krenitsky, T. A. et al. *Biochemistry*, 20, 3615 (1981) and U.S. Pat. No. 4,381,344) were added and the suspension stirred at 35° C. After 120 hours the reaction was filtered and the filtrate chromatographed on a column containing Dowex-I-hydroxide resin (2.5×10 cm). The column was eluted with 90% methanol/water (v/v). Fractions containing product were combined and the solvent removed under vacuum. The residue was dissolved in 30% n-propanol and water (v/v) and chromatographed BioRad P-2 (5×90 cm). The column was eluted with 30% n-propanol/water (v/v). The precipitate from the reaction was re-crystallized from hot methanol yielding 0.352 g that analyzed as 6-cyclopropylaminopurine-9-β-D-arabinofuranoside monohydrate.

Anal. Calcd. for $C_{13}H_{17}N_5O_4 \cdot H_2O$: Calcd: C, 48.00; H, 5.89; N, 21.53. Found: C, 48.05; H, 5.89; N, 21.55.

The filtrate from the recrystallization was chromatographed on BioRad P-2 (5×90 cm) resin as described above. Product containing fractions from both columns were combined and the solvent removed under vacuum yielding 0.342 g of 9-β-D-arabinofuranosyl-6-cyclopropylamino-9 H-purine that analyzed as a 0.8 hydrate with 0.3 $C_3H_8O$. NMR and mass spectrometry were consistent with the structure.

Anal. Calcd. for $C_{13}H_{17}N_5O_4 \cdot 0.8 H_2O \cdot 0.3 C_3H_8O$: Calcd: C, 49.14; H, 6.23; N, 20.61. Found: C, 48.83; H, 5.88; N, 20.29.

EXAMPLE 8:
9-β-D-Arabinofuranosyl-6-ethyl(methyl)amino-9 H-purine

6-Ethyl(methyl)aminopurine was prepared by nucleophilic displacement of the chlorine group on 6-chloropurine (Sigma Chemicals, St. Louis, Mo.) by ethyl-(methyl)amine in acetonitrile. 6-Ethyl(methyl)aminopurine (2.8 mmoles, 0.5 g) and uracil arabinoside (5.6 mmoles, 1.38g) were suspended in 575 ml of a 10 mM potassium phosphate, 0.04% potassium azide solution, pH of 7.4, containing 10% n-propanol (v/v). Purified uridine phosphorylase (6000 I.U.) and purine nucleoside phosphorylase (8400 I.U.) (Krenitsky, T. A. et al., *Biochemistry*, 20, 3615 (1981) and U.S. Pat. No. 4,381,344) were added and the solution stirred at 37° C. Nineteen days later the reaction was filtered and the filtrate chromatographed on a 2.5×13 cm column containing Dowex-1-hydroxide resin. The resin was eluted with 90% methanol/water (v/v). Fractions containing the product were combined and the solvent removed under vacuum. The residue was dissolved in 30% n-propanol/water (v/v) and chromatographed on BioRad P-2 column (7.5×90 cm). Product containing fraction were combined and after lyophilization yielded 0.680 g of 9-β-D-arabinofuranosyl-6-ethyl(methyl)amino-9 H-Purine. NMR and mass spectrometry were consistent with the structure.

Anal. Calcd. for $C_{13}H_{19}N_5O_4$: Calcd: C, 50.48; H, 6.19; N, 22.64. Found: C, 50.36; H, 6.25; N, 22.52.

EXAMPLE 9:
9-β-D-Arabinofuranosyl-2-amino-6-methoxy-9 H-purine

2-Amino-6-methoxypurine (prepared by nucleophilic displacement of the chlorine group on 2-amino-6-chloropurine-(Sigma Chemicals, St. Louis, Mo.) by methanol with sodium hydride in tetrahydrofuran) (6.4 mmoles, 1.05 g) was combined with 35 ml of a uracil arabinoside solution (7.04 mmoles, 1.75 g) in 10 mM potassium phosphate and 7% n-propanol (v/v). The pH was adjusted to 6.75. Purified purine nucleoside phosphorylase (18000 units) and uridine phosphorylase (1020 units) were added and the solution incubated at 37° C. After 26 days the reaction was filtered and the filtrate chromatographed on a column of Dowex-1-formate resin (2×7 cm) after adjusting the pH to 10.5 with concentrated ammonium hydroxide. The column was eluted with 7% n-propanol/water (v/v) and fractions containing product were combined and solvent removed in vacuo. The residue was extracted with 25 ml of water and the filtrate separated from the solids by centrifugation. The supernatant upon standing at ambient temperature formed crystals of 9-β-D-arabinofuranosyl-2-amino-6-methoxy-9 H-purine which after drying in vacuo, yielded 0.327 g of product. NMR and mass spectrometry were consistent with the structure.

Anal. Calcd. for $C_{11}H_{15}N_5O_5$: Calcd: C, 44.44; H, 5.09; N, 23.56. Found: C, 44.49; H, 5.13; N, 23.52.

EXAMPLE 9A:
2-Amino-6-methoxy-9-(5-O-propionyl-β-D-arabinofuranosyl)-9 H-purine 2-Amino-6-methoxy-9-β-D-arabinofuranosyl)-9 H-purine (1.0 g, 3.3 mmol) was suspended in 40 ml of pyridine that contained 300 μL of $H_2O$ and 2 ml of trichloroethyl propionate (Trichloroethyl propionate was synthesized by addition of 19 ml of propionyl chloride (Aldrich) over 30 minutes to 19.1 ml of trichlorethanol (Aldrich) in 40 ml of pyridine at 0° C.). The product was purified by successive washing with 2×100 ml aliquots of $H_2O$, 5% $NaHCO_3$, and $H_2O$. $^1$H NMR (200 MHz, $CDCl_3$), 4.74 (s, 2 H, $Cl_3CH_2$.), 2.49 (q, 2 H, J=7.6 Hz, $CH_3CH_2CO_2$—), 1.21 (t, 3 H, J=7.6 Hz, $CH_3CH_2CO_2$—). The reaction was initiated with 0.100 g of subtilisin (Sigma Chemical Co., St. Louis, Mo., P-5380, lot #38F-0356), which had been activated by dissolving 1 g of the enzyme in 20 ml of 0.1M potassium phosphate at pH 7.8 and lyophilizing to dryness. After stirring for 23 hours at 40° C., the reaction was quenched by filtering off the enzyme and the solvent was removed in vacuo. The crude product was purified by chromatography on a 4.5×25 cm silica gel column with $CH_2Cl_2:CH_3OH$ (9:1) as eluant. Product fractions were pooled and lyophilized from water to yield 0.76 g of the desired product as a white powder; m.p. 124° C.; TLC $R_f$=0.43 (silica gel; $CH_2Cl_2:CH_3OH$ (9:1)); UV $\lambda_{max}$ ($\in$, $mM^{-1}$ $cm^{-1}$) at pH 7.0, 278 nm (9.5). $^1$H NMR(200 MHz, DMSO-$d_6$), δ7.83(s, 1 H, $H_8$), 6.44 (s, 2 H, 2-$NH_2$), 6.14 (s, 1 H, $H_{1'}$), 5.75 (d, 1 H, J=4.3 Hz, 2'-OH), 5.65 (d, 1 H, J=3.5 Hz, 3'-OH), 4.28 (m, 2 H, $H_{2'}$ and $H_{3'}$), 4.08 (m, 2 H, $H_{5'}$), 3.95 (s, 3 H, 6'-$OCH_3$), 3.91 (m, 1 H, H4'), 2.32 (q, 2 H, J=7.6 Hz, $CH_3CH_2CO_2$—), 1.01 (t, 3 H, J=7.5 Hz, $CH_3CH_2CO_2$—); MS (ci) 354 (M+1), 280 (M-$C_2H_5CO_2$).

Anal. Calcd. for $C_{14}H_{19}N_5O_6 \cdot 0.46 H_2O$: Calcd: C, 46.49; H, 5.55; N, 19.36. Found: C, 46.46; H, 5.52; N, 19.45.

EXAMPLE 9B:
2-Amino-6-methoxy-9-(5-O-butyryl-β-D-arabinofuranosyl)-9 H-Purine 2-Amino-6-methoxy-9-β-D-arabinofuranosyl)-9 H-purine (0.50 g, 1.6 mmol) was suspended in 30 ml of pyridine that contained 300 mL of $H_2O$ and 0.52 ml of trichloroethyl butyrate (Trichloroethyl butyrate was synthesized by addition of 47 g of butyryl chloride (Aldrich) over 30 minutes to 67.5 g of trichloroethanol (Aldrich) in 75 mL of pyridine at 0° C.). The product was purified by successive washing with 2×200 mL aliquots of $H_2O$, 5% $NaHCO_3$, and $H_2O$. $^1H$ NMR (200 MHz, $CDCl_3$) 4.74 (s, 2 H, $Cl_3CH_2$_), 2.4 (t, 2 H, J=7.3 Hz, $CH_3CH_2CH_2CO_2$_), 1.72 (sextet, 2 H, J=7.5 Hz, $CH_3CH_2CH_2CO_2$_), 0.99 (t, 3 H, J=7.4 Hz, $CH_3CH_2CH_2CO_2$_)). The reaction was initiated with 0.100 g of subtilisin (Sigma Chemical Co., St. Louis, Mo., P-5380, lot #38F-0356), which had been activated by dissolving 1 g of the enzyme in 20 ml of 0.1M potassium phosphate at pH 7.8 and lyophilizing to dryness. After stirring for 47 hours at 40° C., the reaction was quenched by filtering off the enzyme and the solvent was removed in vacuo. The crude product was purified by chromatography on a 4.5×25 cm silica gel column with $CH_2Cl_2$:$CH_3OH$ (85:15) as the eluant. Product fractions were pooled and lyophilized from water to yield 0.27 g of the desired product as a white powder; m.p. 105° C.; TLC $R_f$=0.65 silica gel; $CH_2Cl_2$:$CH_3OH$ (85:15)); UV $\lambda_{max}$ ($\epsilon$, $mM^{-1}$ $cm^{-1}$) at pH 7.0, 279 nm (8.3). $^1H$ NMR (200 MHz, DMSO-$d_6$): δ7.83 (s, 1 H, $H_8$), 6.46 (s, 2 H, 2-$NH_2$), 6.14 (d, 1 H, J=3.9 Hz, H1'), 5.76 (d, 1 H, J=4.3 Hz, 2'-OH), 5.66(d, 1 H, J=3.7 Hz, 3'-OH), 4.28 (m, 2 H, $H_{2'}$ and $H_{3'}$), 4.07 (m, 2 H, $H_{5'}$), 3.94 (s, 3 H, 6'-$OCH_3$), 3.91 (m, 1 H, $H_{4'}$), 2.28 (t, 2 H, J=7.2 Hz, $CH_3CH_2CH_2CO_2$_), 1.52 (sextet, 2 H, J=7.4 Hz, $CH_3CH_2CH_2CO_2$_), 0.85 (t, 3 H, J=7.3 Hz), $CH_3CH_2CH_2CO_2$_); MS (ci) 368 (M+1).

Anal. Calcd. for $C_{15}H_{21}N_5O_6 \cdot 0.60$ $H_2O$: Calcd: C, 47.64; H, 5.72; N, 18.52. Found: C, 47.62; H, 5.82; N, 18.53.

EXAMPLE 9C:
2-Amino-9-(2,5-di-O-tert-butyldimethylsilyl-β-D-arabinofuranosyl)-6 -methoxy-9 H-purine.

2-Amino-9-(β-D-arabinofuranosyl)-6-methoxy-9 H-purine (10 g, 34 mmol) was added to a 500 mL round bottom flask and dried by coevaporation with pyridine (2×50 mL). Imidazole (11 g, 160 mmol) was added, followed by tert-butyldimethylsilyl chloride (11 g, 74 mmol). The flask was flushed with argon and fitted with a septum. Dry dimethylformamide (DMF, 40 mL) was added and the solution was stirred at room temperature for 18 hours. TLC on silica gel with acetone: $CHCl_3$ (1:10) showed that about 20% of the starting material remained ($R_f$=0.05) and that three higher $R_f$ spots had formed at 0.18, 0.41 and 0.75. Additional tert-butyldimethylsilyl chloride (1.0 g, 6.6 mmol) was added and stirring was continued for 24 hours. TLC in the same solvent subsequently showed all the starting material was consumed.

The DMF was then removed under reduced pressure and the residue was partitioned between ethyl acetate (350 mL) and $H_2O$ (100 mL and 3×50 mL). The aqueous layers were back extracted with ethyl acetate (100 mL) and the combined organic layers were dried ($MgSO_4$), filtered, and concentrated. Crude product was purified on a silica gel flash column (5×25 cm) eluted with a step gradient of acetone in $CHCl_3$ (1:20 to 1:2). Three product fractions were obtained corresponding to the three spots observed by TLC. The $R_f$=0.18 fraction provided 4.0 g (23%) of a white solid identified as the 2,5-disilylated product: m.p.=180°–182° C. (uncorrected); UV $\lambda_{max}$ (95% EtOH): 248.8 nm and 280.8 nm; MS (EI): m/z 468 ($C_{19}H_{34}N_5O_5Si_2$), 450 ($C_{19}H_{32}N_5O_4Si_2$), 336 ($C_{13}H_{18}N_5O_4Si$), 322 ($C_{14}H_{24}N_5O_2Si$), 264 ($C_{10}H_{14}N_5O_2Si$), 222 ($C_8H_8N_5O_3$), 208 ($C_8H_{10}N_5O_2$), 194 ($C_7H_8N_5O_2$), 166 ($C_6H_8N_5O$), 133 ($C_6H_{17}OSi$), 115 ($C_6H_{15}Si$), 57 ($C_4H_9$). $^1H$-NMR ($CDCl_3$): δ7.87 (s, 1 H, H–8), 6.29 (d, 1 H, H–1', J=4.6 Hz), 4.82 (brs, 2 H, $NH_2$), 4.39–4.34 (m, 2 H, H–2' and 3'), 4.07 (s, 3 H, —$OCH_3$), 3.94–3.82 (m, 3 H, H–4' and 5'), 2.40 (brs, 1 H, 3'-OH), 0.91 (s, 9 H, $(CH_3)_3CSi$), 0.71 (s, 9 H, $(CH_3)_3CSi$), 0.09 (s, 6 H, $(CH_3)_2Si$), −0.02 (s, 3 H, $(CH_3)Si$), −0.24 (s, 3 H, $(CH_3)Si$).

Anal. Calcd. for $C_{23}H_{43}N_5O_5Si_2$: Calcd: C, 52.54; H, 8.24; N, 13.32. Found: C, 52.28; H, 8.20; N, 13.17.

EXAMPLE 9D:
2-Amino-9-(2,5-di-O-tert-butyldimethylsilyl-3-O-pivaloyl-β-D-arabinofuranosyl)- 6-methoxy-9 H-purine 2-Amino-9-[(2,5-di-O-tert-butyldimethylsilyl)-β-D-arabinofuranosyl]-6-methoxy-9 H-purine (2.0 g, 3.8 mmol) was weighed in to a flame dried 250 mL round bottom flask. 4-N,N-Dimethylaminopyridine (0.05 g, 0.4 mmol) was added and the flask was flushed with argon and sealed with a septum. Dry acetonitrile (50 mL), triethylamine (8.0 mL), and pivalic anhydride (3 mL, 14.8 mmol) were added to the reaction mixture. After 158 hours, the reaction mixture was concentrated and the residue was taken up in ethyl acetate (250 mL) and extracted with $H_2O$ (3×50 mL). The ethyl acetate was dried ($MgSO_4$), filtered, and concentrated to give 3.8 g of a yellow oil. A 300 mg portion of this material was purified on a Chromatotron (Harrison Scientific) fitted with a 4 mm silica gel rotor, eluting with acetone:$CHCl_3$ (1:10). The product was isolated as a clear gum (0.176 g); MS (EI): m/z 609 ($C_{28}H_{51}N_5O_6Si_2$), 594 ($C_{27}H_{48}N_5O_6Si_2$), 552 ($C_{24}H_{42}N_5O_6Si_2$), 450 ($C_{19}H_{32}N_5O_4Si_2$), 322 ($C_{14}H_{24}N_5O_2Si_2$), 314 ($C_{16}H_{30}O_4Si$), 194 ($C_7H_8N_5O_2$), 166 ($C_6H_8N_5O$), 57 ($C_4H_9$). $^1H$-NMR ($CDCl_3$): δ7.93 (s, 1 H, H–8), 6.25 (d, 1 H, H–1', J=3.8 Hz), 5.28 (d, 1 H, H–3', J=2.2 Hz), 5.05 (brs, 2 H, $NH_2$), 4.30 (dd, 1 H, H–2', $J_{1',2}$=3.6 Hz and $J_{2',3}$=1.8 Hz), 4.10 (s, 3 H, —$OCH_3$), 4.04 (dt, 1 H, H–4', J=2.5 Hz, J=5.9 Hz), 3.19 (d, 2 H, H–5', J=5.5 Hz), 1.27 (s, 9 H, —$OCOC(CH_3)_3$), 0.90 (s, 9 H, —$SiC(CH_3)_3$), 0.75 (s, 9 H, —$SiC(CH_3)_3$), 0.09 (s, 6 H, —$Si(CH_3)_2$), 0.02 (s, 3 H, —$Si(CH_3)$), −0.33 (s, 3 H, —$Si(CH_3)$).

Anal. Calcd. for $C_{28}H_{51}N_5O_6Si_2 \cdot 0.75C_3H_6O \cdot 0.05$ $CHCl_3$: Calcd: C, 55.19; H, 8.49; N, 10.62. Found: C, 55.32; H, 8.61; N, 10.53.

EXAMPLE 9E:
2-Amino-6-methoxy-9-(3-O-pivaloyl-β-D-arabinofuranosyl)-9 H-purine 2-Amino-6- methoxy-9-[(3-O-pivaloyl-2,5-di-O-tert-butyldimethylsilyl)-β-D-arabinofuranosyl]-9 H-purine (2.1 g, 3.4 mmol) was taken up in THF (40 mL) and cooled in an ice bath to 5° C. $H_2O$ (1 mL) was added, followed by tetrabutylammonium fluoride (TBAF) as a 1M solution in THF (10 mL, 10 mmol). After 2 hours at 5° C., an additional 10 mL of TBAF was added. After two hours, the reaction was treated with yet an additional 5 mL of TBAF and allowed to stir for eighteen hours more. The reaction mixture was then diluted with $CHCl_3$ (40 mL) and passed through a pad of silica gel (230–400 mesh, 5×5 cm) with 1:1 acetone:$CHCl_3$ (500 mL). The filtrate was concentrated and added to a silica gel column (230–400 mesh, 5×18 cm). The column was eluted with a step gradient of acetone in $CHCl_3$ (1:10 to 1:1 acetone:$CHCl_3$). Two main fractions were obtained from the column corresponding to material with an $R_f$=0.74 and 0.50 in acetone:$CHCl_3$ (1:1). The lower $R_f$ material was isolated as a white powder 0.77 g (53%) and was shown to be the desired 3'-O-pivaloyl derivative: m.p. 241°–243° C. (uncorrected); UV $\lambda_{max}$ ($\epsilon$): pH=7.00: 278.9 nm (8,700) and 247.7 nm (8,900); 0.1N CHl: 287.0 (8,600) and 243.7 (6,800); 0.1N NaOH: 279.2 (8,900) and 248.7 (8,200); MS (EI): m/z 381 (M, $C_{16}H_{23}N_5O_6$), 366 ($C_{15}H_{20}N_5O_6$), 296 ($C_{11}H_{14}N_5O_5$), 280 ($C_{11}H_{14}N_5O_4$), 250 ($C_{10}H_{12}N_5O_3$), 232 ($C_{10}H_{10}N_5O_2$), 208 ($C_8H_{10}N_5O_2$), 194 ($C_7H_8N_5$ $O_2$), 165 ($C_6H_7N_5O$), 136 ($C_5H_4N_4O$), 85 ($C_5H_9O$); IR (KBr): 1733.6, 1594.7 cm$^{-1}$. $^1$H-NMR (Me$_2$SO-d$_6$): δ7.95 (s, 1 H, H–2), 6.45(brs, 2 H, NH$_2$), 6.10 (d, 1 H, H–1', J=4.3 Hz), 6.10 (d, 1 H, 2'-OH, J=5.5 Hz) 5.16–5.10 (m, 2 H, H–3' and 5'-OH), 4.23–4.20 (m, 1 H, H–2'), 3.94 (s, 3 H, Pur-OCH$_3$), 3.90–3.86 (m, 1 H, H–4'), 3.67–3.60 (m, 2 H, 5'), 1.18 (s, 9 H, C(CH$_3$)$_3$).

Anal. Calcd. for $C_{16}H_{23}N_5O_6$·0.40 CHCl$_3$: Calcd: C, 45.90; H, 5.50; N, 16.32. Found: C, 45.72; H, 5.43; N, 16.04.

EXAMPLE 9F:
2-Amino-9-(3,5-di-O-tert-butyldimethylsilyl-2-O-valeryl-β-D-arabinofuranosyl)- 6-methoxy-9 H-purine 2-Amino-9-[(3,5-di-O-tert-butyldimethylsilyl)-β-D-arabinofuranosyl]-6-methoxy-9 H-purine (1.3 g, 2.5 mmol) was weighed into a flame dried 250 mL round bottom flask. 4-N,N-Dimethylaminopyridine (0.05 g, 0.4 mmol) was added and the flask was flushed with argon and sealed with a septum. Dry acetonitrile (30 mL), triethylamine (5.0 mL) were added and the solution was cooled in an ice bath. Valeric anhydride (0.6 mL, 3.0 mmol) was added to the reaction mixture. After 18 hours at 0°–5° C., the reaction mixture was concentrated and the residue was taken up in hexane:ethyl acetate (1:1) (200 mL) and extracted with H$_2$O (3×50 mL). The organic layer was dried (MgSO$_4$) filtered, and concentrated to give 1.7 g of a yellow oil. A 270 mg portion of this material was purified on a Chromatotron (Harrison Scientific) fitted with a 2 mm silica gel rotor. The rotor was eluted with acetone:CHCl$_3$ (1:10). The product off the Chromatotron was a white solid (0.21 g, 0.34mmol): m.p.=105°–107° C. (uncorrected); MS(EI): m/z 609 ($C_{28}H_{51}N_5O_6Si_2$), 594 ($C_{27}H_{48}N_5O_6Si_2$), 552 ($C_{24}H_{42}N_5O_6Si_2$), 420 ($C_{18}H_{28}N_5O_5Si$), 292 ($C_{13}H_{18}N_5O_3$), 261 ($C_{12}H_{15}N_5O_2$), 231 ($C_{10}H_9N_5O_2$), 194($C_7H_8N_5O_2$), 166 ($C_6H_8N_5O$), 159 ($C_7H_{15}O_2Si$), 57 ($C_4H_9$). $^1$H-NMR (CDCl$_3$): δ7.92 (s, 1 H, H–8), 6.39 (d, 1 H, H–1', J=5.7 Hz), 5.33 (t, 1 H, H–2', J=5.7 Hz), 4.84 (brs, 2 H, NH$_2$), 4.60 (t, 1 H, H–3', J=5.7 Hz), 4.05 (s, 3 H, OCH$_3$), 3.93–3.80 (m, 1 H, H–4' and H–5'), 2.09 (dt, 1 H, C(O)CH$_2$, J=7.5 Hz), 1.94 (dt, 1 H, C(O)CH$_2$, J=7.5 Hz, J=15 Hz), 1.32–1.00 (m, 4H, —CH$_2$CH$_2$—), 0.93 (s, 9 H, —SiC(CH$_3$)$_3$), 0.89 (s, 9 H, —SiC(CH$_3$)$_3$), 0.76 (t, 3 H, —CH$_3$, J=7.0 Hz); 0.11 (s, 3 H, Si(CH$_3$)), 0.09 (s, 3 H, —Si(CH$_3$)), 0.09 (s, 3 H, —Si(CH$_3$)), 0.08 (s, 3 H, —Si(CH$_3$)).

Anal. Calcd. for $C_{28}H_{51}N_5O_6Si_2$: Calcd: C, 55.14; H, 8.43; N, 11.48. Found: C, 55.09; H, 8.45; N, 11.46.

EXAMPLE 9G:
2-Amino-6-methoxy-9-(2-O-valeryl-β-D-arabinofuranosyl)-9 H-purine 2-Amino-9-(3,5-di-O-tert-butyldimethylsilyl- 2-O-valeryl-β- D-arabinofuranosyl)-6-methoxy-9 H-purine (1.4 g, 2.3 mmol) was taken up in tetrahydrofuran (THF, 40 mL) and cooled in an ice bath to 5° C. Acetic acid (0.06 mL, 10 mmol) was added, followed by tetrabutylammonium fluoride (TBAF) as a 1M solution in THF (10 mL, 10 mmol). After 18 hours at 5° C., the reaction mixture was diluted with CCHl$_3$ (40 mL) and passed through a pad of silica gel (230–400 mesh, 5×5 cm) with 1:1 acetone:CHCl$_3$ (500 mL).The filtrate was concentrated and purified on a Chromatotron fitted with a 4 mm rotor and eluted with neat ethyl acetate. Pure product was obtained from the column as a white foam 0.72 g (78%) after drying and was shown to be the desired 2'-O-valeryl derivative: m.p.: 83°–86° C. (uncorrected); UV λ$_{max}$ (ε): pH=7.00: 280.0 nm (7,800), 247.8 nm (8,400); 0.1N HCl: 278.6 (8,000), 248.7 (7,400); 0.1N NaOH: 286.2 (7,600), 244.9 (7,200); MS (EI): m/z 381 ($C_{16}H_{23}N_5O_6$), 351 ($C_{15}H_{21}N_5O_5$), 292 ($C_{13}H_{18}N_5O_3$), 279 ($C_{11}H_{13}N_5O_4$), 249 ($C_{10}H_{11}N_5O_3$), 217 ($C_{10}H_{17}O_5$), 194 ($C_7H_8N_5O_2$), 165 ($C_6H_7N_5O$), 135 ($C_5H_5N_4$), 85 ($C_5H_9O$). IR (KBr) 1745.2, 1613.3 and 1588.7 cm$^{-1}$. $^1$H-NMR (Me$_2$SO-d$_6$): δ7.93 (s, 1 H, H–2), 6.46 (brs, 2 H, NH$_2$), 6.26 (d, 1 H, H–1', J=5.9 Hz), 5.79 (d, 1 H, 3'-OH, J=5.1 Hz), 5.23 (t, 1 H, H–2', J=5.8 Hz), 5.02 (t, 1 H, 5'-OH, J=5.6 Hz), 4.36 (ddd, 1 H, H–3', J$_{3',3'-OH}$=5.1 Hz, J$_{2',3}$=5.7 Hz, J$_{3',4}$=5.8 Hz), 3.93 (s, 3 H, Pur-OCH$_3$), 3.83–3.78 (m, 1 H, H–4'), 3.68–3.61 (m, 2 H, H–5'), 2.09 (dt, 1 H, C(O)CH$_2$, J=7.5 Hz, J=15 Hz), 1.93 (dt, 1 H, C(O)CH$_2$, J=7.5 Hz, J=15 Hz), 1.30–0.90 (m, 4H, —CH$_2$CH$_2$—), 0.65 (t, 3 H, —CH$_3$, J=7 Hz).

Anal. Calcd. for $C_{16}H_{23}N_5O_6$·0.15 $C_5H_{10}O_3$: Calcd: C, 50.41; H, 6.22; N, 17.29. Found: C, 50.41; H, 6.59; N, 17.40.

EXAMPLE 9H:
2-Amino-9-(3-O-benzoyl-2,5-di-O-tert-butyldimethylsilyl-β-D-arabinofuranosyl)-6-methoxy-9 H-purine 2-Amino-9-[(2,5-di-O-tert-butyldimethylsilyl)-β-D-arabinofuranosyl]-6-methoxy-9 H-purine (1.5 g, 2.9 mmol) was weighed into a flame dried 250 mL round bottom flask. 4-N,N-Dimethylaminopyridine (0.05 g, 0.4 mmol) was added and the flask was flushed with argon and sealed with a septum. Dry acetonitrile (50 mL), triethylamine (5.0 mL), and benzoic anhydride (0.77 g, 3.4 mmol) were added to the reaction mixture. After 5 hours at ambient temperature, the reaction mixture was concentrated and the residue was taken up in ethyl acetate (250 mL) and extracted with H$_2$O (2×50 mL). The ethyl acetate was dried (MgSO$_4$), filtered, and concentrated to give 3.8 g of a yellow oil. A 270 mg portion of this material was purified on a Chromatotron (Harrison Scientific) fitted with a 4 mm silica gel rotor. The rotor was eluted with acetone:CHCl$_3$ (1:10). The product off the Chromatotron was a white solid (0.18 g, 0.29 mmol): m.p.=73°–75° C. (uncorrected); MS (EI): m/z 630 ($C_{30}H_{48}N_5O_6Si_2$), 614 ($C_{29}H_{44}N_5O_6Si_2$), 572 ($C_{26}H_{44}N_5O_6Si_2$), 451 ($C_{19}H_{33}N_5O_4Si_2$), 194 ($C_7H_8N_5O_2$), 179 ($C_6H_5N_5O_2$), 166 ($C_6H_8N_5O$), 105 ($C_7H_5O$). $^1$H-NMR (CDCl$_3$): δ8.12–8.07 (m, 2 H, Ar-H), 7.92 (s, 1 H, H–8), 7.63–7.45 (m, 3 H, Ar-H), 6.33 (d, 1 H, H–1', J=3.7 Hz), 5.46 (t, 1 H, H–3', J=1.8 Hz), 4.79 (brs, 2 H, NH$_2$), 4.42 (dd, 1 H, H–2', J$_{1',2}$=3.7 Hz and J$_{2',3}$=1.7 Hz), 4.30–4.20 (m, 1 H, H–4'), 4.07 (s, 3 H, —OCH$_3$), 3.99–3.95 (m, 2 H, H–5'), 0.89 (s, 9 H, —SiC(CH$_3$)$_3$), 0.76 (s, 9 H, —Si(CH$_3$)$_3$), 0.09 (s, 6 H, —Si(CH$_3$)$_2$), 0.03 (s, 3 H, —Si(CH$_3$)), −0.34 (s, 3 H, —Si(CH$_3$)):

Anal. Calcd. for $C_{30}H_{47}N_5O_6Si_2$: Calcd: C, 57.20; H, 7.52; N, 11.12. Found: C, 57.08; H, 7.59; N, 11.05.

EXAMPLE 9I:
2-Amino-9-(3-O-benzoyl-β-D-arabinofuranosyl)-6-methoxy-9 H-purine 2-Amino-9-(3-O-benzoyl-2,5-di-O-tert-butyldimethylsilyl)-β-D-arabinofuranosyl]-6 -methoxy-9 H-purine (1.97 g, 2.6 mmol) was taken up in tetrahydrofuran (THF, 40 mL)

and cooled in an ice bath to 5° C. Acetic acid (0.06 mL, 10 mmol) was added, followed by tetrabutylammonium fluoride (TBAF) as a 1M solution in THF (10 mL, 10 mmol). After 18 hours at 5° C., the reaction mixture was diluted with CHCl$_3$ (40 mL) and passed through a pad of silica gel (230–400 mesh, 5×5 cm) with 1:1 acetone:CHCl$_3$ (500 mL). The filtrate was concentrated to a white solid which was adsorbed onto 10 g of silica gel and added to a silica gel column (230–400 mesh, 5×18 cm). The column was eluted with acetone:CHCl$_3$ (1:2). Pure product was obtained from the column corresponding to material with an R$_f$=0.56 in acetone:CHCl$_3$ (1:1). This material was a white powder 0.77 g (1.9 mmol) after drying and was shown to be the desired 3'-O-benzoyl derivative: rep. 155°–157° C. (uncorrected); UV $\lambda_{max}$ ($\in$): pH=7.00: 278.3 nm (10,100), 235.2 nm (18,800); 0.1N HCl: 278.1 (9,100), 245 (sh) (9,600); 0.1N NaOH: 284.8(9,600), 233.9 (18,400); MS (EI): m/z 401 (M, C$_{18}$H$_{19}$N$_5$O$_6$), 296 (C$_{11}$H$_{14}$N$_5$O$_5$), 250 (C$_{10}$H$_{12}$N$_5$O$_3$), 232 (C$_{10}$H$_{10}$N$_5$O$_2$), 20 (C$_8$H$_{10}$N$_5$ O$_2$), 194 (C$_7$H$_8$N$_5$O$_2$), 179 (C$_7$H$_7$N$_4$O$_2$), 165 (C$_6$H$_7$N$_5$O), 136 (C$_5$H$_4$N$_5$), 122 (C$_7$H$_5$O$_2$), 105 (C$_7$H$_5$ O); IR(KBr): 1714.6, 1611.8 and 1591.7 cm$^{-1}$. $^1$H-NMR(Me$_2$SO-d$_6$): $\delta$8.06(s, 1 H, H–2), 8.02–8.00 (m, 2 H, Ar-H), 7.71 (t, 1 H, Ar-H, J=7.3 Hz), 7.57 (t, 2 H, Ar-H, J=7.4 Hz), 6.45 (brs, 2 H, NH$_2$), 6.20 (d, 1 H, H–1', J=4.3 Hz), 6.12 (d, 1 H, 2'-OH, J=5.5 Hz), 5.41 (t, 1 H, H–3', J=2.9 Hz), 5.20 (t, 1 H, 5'-OH, J=5.5 Hz), 4.43–4.37 (m, 1 H, H–2'), 4.17–4.11 (m, 1 H, H–4'), 3.95 (s, 3 H, Pur-OCH$_3$), 3.79–3.72 (m, 2 H, 5').

Anal. Calcd. for C$_{18}$H$_{19}$N$_5$O$_6$.0.60 C$_3$H$_6$O.0.05CHCl$_3$:Calcd: C, 53.92; H, 5.16; N, 15.84. Found: C, 53.81; H, 5.10; N, 15.76.

EXAMPLE 9J:
2-Amino-9-(3,5-di-O-tert-butyldimethylsilyl-β-D-arabinofuranosyl)-6 -methoxy-9 H-purine 2-Amino-9-(β-D-arabinofuranosyl)-6-methoxy-9 H-purine (10 g, 34 mmol) was added to a 500 mL round bottom flask and dried by coevaporation with pyridine (2×50 mL). Imidazole (11 g, 160 mmol) was added, followed by tert-butyldimethylsilyl chloride (11 g, 74 mmol). The flask was flushed with argon and fitted with a septum. Dry dimethylformamide (DMF, 40 mL) was added and the solution was stirred at room temperature for 18 hours. TLC on silica gel with acetone:CHCl$_3$ (1:10) showed that about 20% of the starting material remained (R$_f$=0.05) and that three higher R$_f$ spots had formed at 0.18, 0.41 and 0.75. Additional tert-butyldimethylsilyl chloride (1.0 g, 6.6 mmol) was added and stirring was continued for 24 hours. TLC in the same solvent subsequently showed all the starting material was consumed.

The DMF was then removed under reduced pressure and the residue was partitioned between ethyl acetate (350 mL) and H$_2$O (100 mL and 3×50 mL). The aqueous layers were back extracted with ethyl acetate (100 mL) and the combined organic layers were dried (MgSO$_4$), filtered, and concentrated. Crude product was purified on a silica gel flash column (5×25cm) eluted with a step gradient of acetone in CHCl$_3$ (1:20to 1:2). Three product fractions were obtained corresponding to the three spots observed by TLC. The R$_f$=0.41 fraction provided 8.0 g (45 %) of a white solid identified as the 3,5-disilylated product: m.p.=88–90° C. (uncorrected); UV $\lambda_{max}$ (95% EtOH): 247.1 nm and 280.1 nm; MS (EI): m/z 526 (M+H, C$_{23}$H$_{44}$N$_5$O$_5$Si$_2$), 510 (C$_{22}$H$_{40}$N$_5$O$_5$Si$_2$), 468 (C$_{19}$H$_{34}$N$_5$O$_5$Si$_2$), 336 (C$_{13}$H$_{18}$N$_5$O$_4$Si), 301 (C$_{13}$H$_{25}$O$_4$Si$_2$), 261 (C$_{11}$H$_{11}$N$_5$O$_3$), 231 (C$_{10}$H$_9$N$_5$O$_2$), 208 (C$_8$H$_{10}$N$_5$O$_2$), 194 (C$_7$H$_8$N$_5$O$_2$), 165 (C$_6$H$_7$N$_5$O), 133 (C$_6$H$_{17}$OSi), 115 (C$_6$H$_{15}$Si), 57 (C$_4$H$_9$). $^1$H-NMR (CDCl$_3$): $\delta$8.01 (s, 1 H, H–8), 6.16(d, 1 H, H–1', J=3.1 Hz), 5.08(brs, 1 H, 2'-OH), 4.84(brs, 2 H, NH$_2$), 4.31 (t, 1 H, H–3', J=1.8 Hz), 4.16–4.13 (m, 1 H, H–2'), 4.05 (s, 3 H, —OCH$_3$), 4.02–3.99 (m, 1 H, H–4'), 3.94 (dd, 1 H, H–5', J$_{4',5'}$=3.7 Hz, J$_{5',5''}$=11.0 Hz), 3.79 (dd, 1 H, H–5'', J$_{4',5}$=2.7 Hz, J$_{5',5''}$=11.0 Hz), 0.94 (s, 9 H, (CH$_3$)$_3$CSi), 0.93 (s, 9 H, (CH$_3$)$_3$CSi), 0.17 (s, 3 H, CH$_3$Si ), 0.14 (s, 3 H, CH$_3$Si ), 0.12 (s, 6 H, (CH$_3$)$_2$Si).

Anal. Calcd. for C$_{23}$H$_{43}$N$_5$O$_5$Si$_2$: Calcd: C, 52.54; H, 8.24; N, 13.32. Found: C, 52.32; H, 8.24; N, 13.25.

EXAMPLE 9K:
2-Amino-9-(3,5-di-O-tert-butyldimethylsilyl-2-O-pivaloyl-β-D-arabinofuranosyl)- 6-methoxy-9 H-purine 2-Amino-9-(3,5-di-O-tert-butyldimethylsilyl-β-D-arabinofuranosyl)-6-methoxy-9 H-purine (1.3 g, 2.5 mmol) was weighed into a flame dried 250 mL round bottom flask. 4-N,N-Dimethylaminopyridine (0.05 g, 0.4 mmol) was added and the flask was flushed with argon and sealed with a septum. Dry acetonitrile (30 mL), triethylamine (50 mL) and pivalic anhydride (0.6 mL, 3.0 mmol) were added to the reaction mixture which was stirred at room temperature. After 160, the reaction mixture was concentrated, the residue taken up in ethyl acetate (250 mL) and extracted with H$_2$O (3×50 mL). The ethyl acetate was collected, dried (MgSO$_4$), filtered, and concentrated to give 2.0 g of a yellow oil. A 250 mg portion of this material was purified on a Chromatotron® (Harrison Scientific) fitted with a 2 mm silica gel rotor, eluted with acetone:CHCl$_3$ (1:10). The product off the Chromatotron® was a clear gum (0.176 g); MS (EI): m/z 609 (C$_{28}$H$_{51}$N$_5$O$_6$Si$_2$), 594 (C$_{27}$H$_{48}$N$_5$O$_6$Si$_2$), 552 (C$_{24}$H$_{42}$N$_5$O$_6$Si$_2$), 420 (C$_{18}$H$_{28}$N$_5$O$_5$Si), 292 (C$_{13}$H$_{18}$N$_5$O$_3$), 261 (C$_{12}$H$_{15}$N$_5$O$_2$), 231 (C$_{10}$H$_9$N$_5$O$_2$), 194 (C$_7$H$_8$N$_5$O$_2$), 166 (C$_6$H$_8$N$_5$O), 159 (C$_7$H$_{15}$O$_2$Si), 57 (C$_4$H$_9$). $^1$H-NMR (CDCl$_3$): $\delta$7.88 (s, 1 H, H–8), 6.40 (d, 1 H, H–1', J=5.9 Hz), 5.30 (t, 1 H, H–2', J=6.0 Hz), 4.85 (br.s, 2 H, NH$_2$), 4.65 (t, 1 H, H–3', J=6.0 Hz), 4.04 (s, 3 H, OCH$_3$), 3.95–3.85 (m, 1 H, H–4' and H–5'), 0.92 (s, 9 H, OCOC(CH$_3$) $_3$), 0.89 (s, 9 H, SiC(CH$_3$)$_3$), 0.88 (s, 9 H, SiC(CH$_3$)$_3$), 0.13 (s, 3 H, SiCH$_3$), 0.11 (s, 3 H, SiCH$_3$), 0.08 (s, 3 H, SiCH$_3$), 0.07 (s, 3 H, SiCH$_3$).

Anal. Calcd. for C$_{28}$H$_{51}$N$_5$O$_6$Si$_2$: Calcd: C, 55.14; H, 8.43; N, 11.48. Found: C, 54.97; H, 8.42; N, 11.10.

EXAMPLE 9L:
2-Amino-6-methoxy-9-[(2-O-pivaloyl)-β-D-arabinofuranosyl]-9 H-purine 2-Amino-6-methoxy-9-(3,5-di-O-tert-butyldimethylsilyl-2 -O-pivaloyl-β-D-arabinofuranosyl)- 9 H-purine (1.3 g, 2.0 mmol) was taken up in tetrahydrofuran (THF, 40 mL) and cooled in an ice bath to 5° C. Acetic acid (0.06 mL, 10 mmol) was added, followed by tetrabutylammonium fluoride as a 1M solution in THF (10 mL, 10 mmol). After 24 hours at 5° C., the reaction mixture was diluted with CHCl$_3$ (40 mL) and passed through a pad of silica gel (230–400 mesh, 5×5 cm) with 1:1 acetone:CHCl$_3$ (500 mL). The filtrate was concentrated and applied to a silica gel column (230–400 mesh, 5×18 cm), eluted with acetone:CHCl$_3$ (1:2, 1.5 L), followed by acetone:CHCl$_3$ (1:1, 1.5 L). Pure product was obtained from the column as a white powder 0.76 g (100%) after drying and was shown to be the desired 2'-O-pivaloyl derivative: m.p.: 83°–85° C. (uncorrected); UV $\lambda_{max}$ ($\in$): pH=7.00: 279.7 nm (8,100), 247.9 nm (8,800);

0.1N CHl: 286.6 (7,300), 244.7 (6,200); 0.1N NaOH: 279.7 (8,000), 248.8 (7,900); MS (EI): m/z 250 ($C_{10}H_{12}N_5O_3$), 232 ($C_{10}H_{10}N_5O_2$), 217 ($C_{10}H_{17}N_5$), 208 ($C_8H_{10}N_5O_2$), 194 ($C_7H_8N_5O_2$), 165 ($C_6H_7N_5O$), 135 ($C_5H_4N_4O_4$), 101 ($C_5H_9O_2$), 85 ($C_5H_9O$); IR (KBr): 1734.2, 1616.3 and 1589.4 cm$^{-1}$; $^1$H-NMR (Me$_2$SO-d$_6$): δ7.97 (s, 1 H, H–2), 6.47 (br.s, 2 H, NH$_2$), 6.26 (d, 1 H, H–1', J=5.9 Hz), 5.79 (d, 1 H, 3'-OH, J=5.3 Hz), 5.23 (dd, 1 H, H–2', J$_{1',2}$=5.9 Hz, J$_{2',3}$=5.2 Hz), 5.06 (t, 1 H, 5'-OH, J=5.5 Hz), 4.37 (ddd, 1 H, H–3', J$_{3',3}$=5.3 Hz, J$_{2',3}$=5.2 Hz), J$_{3',4}$=6.9 Hz), 3.92 (s, 3 H, Pur-OC$\underline{H}_3$), 3.84–3.79 (m, 1 H, H–4'), 3.68–3.62 (m, 2 H, H–5').

Anal. Calcd. for $C_{16}H_{23}N_5O_6$·0.40 CHCl$_3$: Calcd: C, 45.90; H, 5.50; N, 16.32. Found: C, 46.03; H, 5.69; N, 16.03.

EXAMPLE 9M: 2-Amino-9-(2-O-benzoyl-3,5-di-O-tert-butyldimethylsilyl-β-D-arabinofuranosyl)-6-methoxy-9 H-purine 2-Amino-9-[(3,5-di-O-tert-butyldimethylsilyl)-β-D-arabinofuranosyl]-6-methoxy-9 H-purine (1.3 g, 2.5 mmol) was weighed in to a flame dried 250 mL round bottom Flask. 4-N,N-Dimethylaminopyridine (0.05 g, 0.4 mmol) and benzoic anhydride (0.67 g, 3.0 mmol) were added and the flask was flushed with argon and sealed with a septum. Dry acetonitrile (30 mL) and triethylamine (5.0 mL) were then added, and the mixture stirred at room temperature. After 18 hours, the reaction mixture was concentrated and the residue was taken up in ethyl acetate (250 mL) and extracted with H$_2$O (3×50 mL). The ethyl acetate was dried (MgSO$_4$), filtered, and concentrated to give 1.76 g of a yellow oil. A 250 mg portion of this material was purified on a Chromatotron® (Harrison Scientific) fitted with a 2 mm silica gel rotor. The rotor was eluted with acetone: CHCl$_3$ (1:10). The product off the Chromatotron® was a white solid (0.21 g); m.p.: 129°–131° C. (uncorrected); MS (EI): m/z 629 ($C_{30}H_{47}N_5O_6Si_2$), 572 ($C_{26}H_{47}N_5O_6Si_2$), 440 ($C_{20}H_{22}N_5O_5Si$), 312 ($C_{15}H_{14}N_5O_3$), 261 ($C_{11}H_{25}O_3Si_2$), 231 ($C_9H_{19}O_3Si_2$), 194 ($C_7H_8N_5$ ($_2$), 166 ($C_6H_8N_5O$), 105 ($C_7H_5O$). $^1$H-NMR (CDCl$_3$): δ8.07 (s, 1 H, H–8), 7.67 (dd, 2 H, Ar-H, J=1.0 Hz, J=8.2 Hz), 7.50 (tt, 1 H, Ar-H, J=2.0 Hz, J=8.0 Hz), 7.30 (t, 2 H, Ar-H, J=7.5 Hz), 6.48(d, 1 H, H–1', J=5.5 Hz), 5.63 (t, 1 H, H–2', J=5.5 Hz), 4.74 (t, 1 H, H–3', J=5.6 Hz), 4.68 (br.s, 2 H, NH$_2$), 3.98 (s, 3 H, —OCH$_3$), 4.00–3.80 (m, 3 H, H–4' and H–5'), 0.92 (s, 9 H, —SiC(CH$_3$)$_3$), 0.88 (s, 9 H, —SiC(CH$_3$)$_3$), 0.12 (s, 3 H, —Si(CH$_3$)), 0.09 (s, 3 H, —Si(CH$_3$)), 0.08 (s, 3 H, —Si(CH$_3$)), 0.06 (s, 3 H, —Si(CH$_3$)).

Anal. Calcd. for $C_{30}H_{47}N_5O_6Si_2$:Calcd: C, 57.20; H, 7.52; N, 11.12. Found: C, 57.42; H, 7.57; N, 11.12.

EXAMPLE 9N: 2-Amino-9-(2-O-benzoyl-β-D-arabinofuranosyl)-6-methoxy-9 H-purine

2-Amino-9-[(2-O-benzoyl-3,5-di-O-tert-butyldimethylsilyl)-β-D-arabinofuranosyl]-6-methoxy-9 H-purine (1.26 g, 2.0 mmol) was taken up in tetrahydrofuran (THF, 40 mL) and cooled in an ice bath to 5° C. Acetic acid (0.06 mL, 10 mmol) was added, followed by tetrabutylammonium fluoride (TBAF) as a 1M solution in THF (10 mL, 10 mmol). After 24 hours at 5° C., the reaction mixture was diluted with CHCl$_3$ (40 mL) and passed through a pad of silica gel (230–400 mesh, 5×5 cm) with 1:1 acetone:CHCl$_3$ (500 mL). The filtrate was concentrated and applied to a silica gel column (230–400 mesh, 5×18 cm). The column was eluted with acetone:CHCl$_3$ (1:2, 1 L) followed by acetone:CHCl$_3$ (1:1, 1.5 L). Pure product was obtained from the column corresponding to material with an R$_f$=0.33 in acetone:CHCl$_3$ (1:1). This material was a white powder 0.74 g (90%) after drying and was shown to be the desired 2'-O-benzoyl derivative: m.p.: 82°–84° C. (uncorrected); UV $\lambda_{max}$ (∈): pH=7.00: 279.1 nm (8,600), 237.5 nm (17,800); 0.1N HCl: 277.8 (10,000), 245 (sh) (10,800); 0.1N NaOH: 286.1 (7,600), 236.4 (17,000). MS (EI): m/z 401 (M, $C_{18}H_{19}N_5O_6$), 371 ($C_{17}H_{17}N_5O_5$), 312 ($C_{15}H_{14}N_5O_3$), 279 ($C_{11}H_{13}N_5O_4$), 237 ($C_{12}H_{13}O_5$), 220 ($C_{12}H_{12}N_4$), 208 ($C_8H_{10}N_5O_2$), 194 ($C_7H_8N_5O_2$), 165 ($C_6H_7N_5O$), 135 ($C_5H_5N_5$), 105 ($C_7H_5O$); IR(KBr): 1725.3, 1613.6 and 1588.9 cm$^{-1}$; $^1$H-NMR(Me$_2$SO-d$_6$): δ8.04(s, 1 H, H–2), 7.70–7.57 (m, 3 H, Ar-H), 7.47–7.39 (m, 2 H, Ar-H), 6.44 (br.s, 2 H, NH$_2$), 6.39 (d, 1 H, H–1', J=5.6 Hz), 5.90 (d, 1 H, 3'-OH, J=4.9 Hz), 5.48 (t, 1 H, H–2', J=5.3 Hz), 5.07 (t, 1 H, 5'-OH, J=5.6 Hz), 4.51 (apparent quartet, 1 H, H–3', J$_{3',3'}$-OH=4.9 Hz, J$_{2',3}$=5.6 Hz, J$_{3',4}$=5.1 Hz), 3.87 (s, 3 H, Pur-OC$\underline{H}_3$), 3.94–3.83 (m, 1 H, H–4'), 3.77–3.66 (m, 2 H, H–5').

Anal. Calcd. for $C_{18}H_{19}N_5O_6$·0.20 $C_3H_6O$·0.50 CHCl$_3$: Calcd: C, 48.53; H, 4.41; N, 14.82. Found: C, 48.68; H, 4.54; N, 14.96.

EXAMPLE 9O: 2-Amino-6-methoxy-9-(5-O-valeryl-β-D-arabinofuranosyl)- 9 H-purine

2-Amino-6-methoxy-9-β-O-arabinofuranosyl-9 H-purine (1.0 g, 3.2 mmol) was suspended in 40 ml of pyridine that contained 300 μL of H$_2$O and 2.0 mL of trichloroethyl valerate (Trichloroethyl valerate was synthesized by addition of 36 g of valeryl chloride (Aldrich) over 30 minutes to 45 g of trichloroethanol (Aldrich) in 50 mL of pyridine at 0° C. The product was purified by successive washing with 2×250 ml aliquots of H$_2$O, 5% NaHCO$_3$, and H$_2$O, $^1$H-NMR (200 MHz, CDCl$_3$): δ4.74 (s, 2 H, Cl$_3$CH$_2$—), 2.48 (t, 2 H, J=7.6 Hz, CH$_3$CH$_2$CH$_2$C$\underline{H}_2$CO$_2$—), 1.68 (m, 2 H, CH$_3$CH$_2$C$\underline{H}_2$CH$_2$CO$_2$—), 1.53 (M, 2 H, CH$_3$C$\underline{H}_2$CH$_2$CH$_2$CO$_2$—), 0.93 (t, 3 H, J=7.2 Hz, C$\underline{H}_3$CH$_2$CH$_2$CH$_2$CO$_2$—)). The reaction was initiated with 0.100 g of subtilisin (Sigma Chemical Co., St. Louis, Mo., P-5380, lot #38F-0356), which had been activated by dissolving 1 g of the enzyme in 20 ml of 0.1M potassium phosphate at pH 7.8 and lyophilizing to dryness. After stirring for 24 hours at 40° C., the reaction was quenched by filtering off the enzyme and the solvent was removed in vacuo. The crude product was purified by chromatography on a 4.5×25 cm silica gel column with CH$_2$Cl$_2$:CH$_3$OH (90:10) as the eluant. Product fractions were pooled and lyophilized from water to yield 0.85 g of the desired product as a white powder; m.p. 105° C.; TLC R$_f$=0.39(silica gel; CH$_2$Cl$_2$:CH$_3$OH (90:10)); UV $\lambda_{max}$ (∈, mM$^{-1}$ cm$^{-1}$) at pH 7.0, 279 nm (9.3); MS (Cl) 382 (M+1), 280 (M-C$_5$H$_9$CO$_2$). $^1$H-NMR (200 MHz, DMSO-d$_6$): δ7.83 (s, 1 H, H$_8$), 6.45 (s, 2 H, 2-NH$_2$), 6.15 (d, 1 H, J=3.7 Hz, H$_1$'), 5.76 (d, 1 H, J=4.2 Hz, 2'-OH), 5.65 (d, 1 H, J=3.5 Hz, 3'OH), 4.28 (m, 2 H, H$_2$' and H$_3$'), 4.08 (m, 2 H H$_5$'), 3.94 (s, 3 H, —OCH$_3$) 3.92 (m, 1 H, H$_4$'), 2.29 (t, 2 H, J=7.1 Hz, CH$_3$CH$_2$C$\underline{H}_2$CO$_2$—), 1.49 (m, 2 H, CH$_3$C$\underline{H}_2$CH$_2$CH$_2$CO$_2$—) 1.28 (m, 2 H CH$_3$ C$\underline{H}_2$CH$_2$CH$_2$CO$_2$—), 0.83 (t, 3 H, J=7.2 Hz, C$\underline{H}_3$CH$_2$CH$_2$CH$_2$CO$_2$—).

Anal. Calcd. for $C_{16}H_{23}N_5O_6$·0.36 H$_2$O: Calcd: C, 49.54; H, 6.16; N, 18.05. Found: C, 49.52; H, 6.15; N, 18.10.

EXAMPLE 9P: 2-Amino-6-methoxy-9-(5-O-acetyl-β-D-arabinofuranosyl)-9 H-purine

2-Amino-6-methoxy-9-b-D-arabinofuranosyl-9 H-purine (1.0 g, 3.3 mmol) was suspended in 40 ml of pyridine that contained 300 μL of H₂O and 1 ml of trichloroethyl propionate (Trichloroethyl acetate was synthesized as follows: 2,2,2-trichloroethanol (19.1 mL, 197.1 mmole) and dry pyridine (40 mL) were placed in a three-neck, round-bottom flask equipped with argon inlet valve, thermometer, dropping funnel, magnetic stirring, and ice/H₂O bath. Acetyl chloride (14.5 mL, 199.8 mmole) was placed in the dropping funnel and added over a ten minute period, keeping the temperature below 25° C. while stirring under argon. The resulting product was washed with H₂O (2×100 mL), 5% NaHCO₃ (2×100 mL), and H₂O (2×100 mL). The organic layer was dried over MgSO₄, then filtered through Whatman #1 paper, and distilled under vacuum. A middle cut of 5.18 g was the desired material, contaminated with a small amount of acetic acid: ¹H-NMR (CDCl₃): δ4.73 Cs, 2 H, CH₂O), 2.20 Cs, 3 H, CH₃CO); MS (Cl, CH₄): m/z 197 (M+H, $C_4H_5O_2{}^{37}Cl_3$), 195 (M+H, $C_4H_5O_2{}^{37}Cl_2{}^{35}Cl$), 193 (M+H, $C_4H_5O_2O{}^{35}Cl_2{}^{37}Cl$), 191 (M+H, $C_4H_5O_2{}^{35}Cl_3$), 159 (195-HCl, $C_4H_4O_2{}^{37}Cl_2$), 157 (193-HCl, $C_4H_4O_2{}^{37}Cl{}^{35}Cl$), 155 (191-HCl, $C_4H_4O_2{}^{35}Cl_2$); (EI): m/z 195 (M+H), 193 (M+H), 191 (M+H), 157 (193-CHl), 155 (191-HCl). Analysis for $C_4H_5Cl_3O_2+0.054$ mole $CH_3COOH$: C, 25.35; H, 2.70; Cl, 54.62. Found: C, 25.57; H, 2.72; Cl, 54.66.). The reaction was initiated with 0.050 g of subtilisin (Sigma Chemical Co., St. Louis, Mo., P-5380, lot#38F-0356,), which had been activated by dissolving 1 g of the enzyme in 20 ml of 0.1M potassium phosphate at pH 7.8 and lyophilizing to dryness. After stirring for 23 hours at 40° C. an additional 50 mg of subtilisin and 2 mL of trichloroethyl acetate were added to the reaction. After stirring at 40° for an additional 24 hours the reaction was quenched by filtering off the enzyme and the solvent was removed in vacuo. The crude product was purified by chromatography on a 4.5×25 cm silica gel column with CH₂Cl₂:CH₃OH (9:1) as eluant. Product fractions were pooled and lyophilized from water to yield 0.28 g of the desired product as a white powder. TLC $R_f$=0.35 (silica gel; CH₂Cl₂:CH₃OH (9:1)); UV $\lambda_{max}$ (∈, mM⁻¹ cm⁻¹) at pH 7.0, 279 nm (8.8). ¹H-NMR (200 MHz, DMSO-d₆): δ7.83 (s, 1 H, H₈), 6.45 (s, 2 H, 2-NH₂), 6.14 (d, 1 H, J=3.7 Hz, H₁·), 5.75 (d, 1 H, J=4.5 Hz, 2'-OH), 5.65(d, 1 H, J=3.7 Hz, 3'-OH), 4.26 (m, 2 H, H₂· and H₃·), 4.07 (m, 2 H, H₅·) 3.94 (s, 3 H, —OCH₃) 3.92 (m, 1 H, H₄·), 2.01 (s, 3 H, CH₃CO₂—); MS (Cl) 340 (M+1), 280 (M-CH₃CO₂).

Anal. Calcd. for $C_{14}H_{19}N_5O_6 \cdot 0.52 H_2O$: Calcd: C, 44.77; H, 5.22; N, 20.12. Found: C, 44.79; H, 5.21; N, 20.09.

EXAMPLE 9Q:
2-Amino-6-methoxy-9-(5-O-(4-methoxy-4-oxobutyryl)-β-D-arabinofuranosyl)- 9 H-purine 2-Amino-6-methoxy-9-β-D-arabinosuranosyl-9 H-purine (1.0 g, 3.2 mmol) was suspended in 40 mL of pyridine that contained 300 μL of H₂O and 2 ml of trichloroethyl methylsuccinate. (Trichloroethyl methylsuccinate was synthesized by addition of 25 g of 3-carbomethoxypropionyl chloride (Aldrich) over 30 minutes to 15.8 g of trichloroethanol (Aldrich) in 40 ml of pyridine at 0° C. The product was purified by successive washing with 2×200 ml aliquots of H₂O, 5% NaHCO₃, and H₂O and then dried over Na₂SO₄. ¹H-NMR (200 MHz, CDCl₃): δ4.75 (s, 2 H, Cl₃CH₂—), 3.7 (s, 3 H, CH₃OC(O).), 2.77 (m, 4 H, —OC(O)CH₂CH₂CO₂—)). The reaction was initiated with 0.050 g of subtilisin (Sigma Chemical Co., St. Louis, Mo., P-5380, lot #38F-0356), which had been activated by dissolving 1 g of the enzyme in 20 ml of 0.1M potassium phosphate at pH 7.8 and lyophilizing by filtering off the enzyme and the solvent was removed in vacuo. The crude product was purified by chromatography on a 4.5×25 cm silica gel column with CH₂Cl₂:CH₃OH (90:10) as the eluant. Product fractions were pooled and lyophilized from water to yield 1.01 g of the desired product as a white powder. TLC $R_f$=0.31 (silica gel; CH₂Cl₂:CH₃OH (90:10)); UV $\lambda_{max}$ (∈, mM⁻¹ cm⁻¹) at pH 7.0, 277 nm (9.6). ¹H-NMR (200 MHz, DMSO-d₆): δ7.83 (s, 1 H, H₈), 6.45 (s, 2 H, 2-NH₂), 6.15 (d, 1 H, J=3.7 Hz, H₁·), 5.75 (d, 1 H, J=4.3 Hz, 2'-OH), 5.65 (d, 1 H, J=3.7 Hz, 3'-OH), 4.28 (m, 2 H, H₂· and H₃·), 4.08 (m, 2 H, H₅·), 3.95 (s, 3 H, —OCH₃) 3.91 (m, 1 H, H₄·), 3.51 (s, 3 H, CH₃OC(O)—), 2.56 (s, 4H, —OC(O)CH₂CH₂C(O)O—); MS (Cl) 412 (M+1), 280 (M-C₅H₇O₄).

Anal. Calcd. for $C_{16}H_{21}N_5O_8 \cdot 0.40 H_2O$: Calcd: C, 45.64; H, 5.28; N, 16.63. Found: C, 45.62; H, 5.21; N, 16.67.

EXAMPLE 10:
9-β-D-Arabinofuranosyl-6-n-propoxy-9 H-purine 6-n-Propoxypurine (5.6 mmoles, 1 g, Sigma Chemicals, St. Louis Mo.) was combined with 545 ml of a uracil arabinoside solution (10.1 mmoles)in 10 mM potassium phosphate and 7% n-propanol (v/v). Purified uridine phosphorylase (680 I.U.) and purine nucleoside phosphorylase (12000 I.U.) were added and the reaction stirred at 35° C. The reaction was filtered after 58 days and the filtrate stored at 3° C. for 20 hours. The resulting precipitate was collected by centrifugation, dissolved in 30% n-propanol/water (v/v), and chromatographed on a column of Dowex-1-formate resin (2.5×5 cm) after adjusting the pH to 10.5 with concentrated ammonium hydroxide. The column was eluted with 30% n-propanol/water (v/v) and fractions containing product were combined and solvent removed in vacuo. The residue was dissolved in n-propanol and chromatographed on a column containing BioRad P-2 (5×90 cm). The column was eluted with 30% npropanol/water (v/v). Product-containing fractions were combined and after removing the solvent under vacuum the residue was dissolved in water and chromatographed on a column containing BioRad P-2 (5×90 cm). The column was eluted with water. Product containing fractions were combined and after lyophilization, yielded 0.758 g of 9-β-D-arabinofuranosyl- 6-n-propoxy-9 H-purine that analyzed as a monohydrate. NMR and mass spectrometry were consistent with the structure.

Anal. Calcd. for $C_{13}H_{18}N_4O_5 \cdot H_2O$: Calcd: C, 47.56; H, 6.14; N, 17.06. Found: C, 47.63; H, 6.13; N, 17.11.

EXAMPLE 11: Tablet Formulations

The following formulations A and B are prepared by wet granulation of the ingredients with a solution of povidone, followed by addition of magnesium stearate and compression.

|  | mg/tablet | mg/tablet |
| --- | --- | --- |
| Formulation A | | |
| (a) Active Ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |
| Formulation B | | |
| (a) Active Ingredient | 250 | 250 |
| (b) Lactose B.P. | 150 | — |
| (c) Avicel PH 101 | 60 | 26 |

-continued

| | | |
|---|---|---|
| (d) Povidone B.P. | 15 | 9 |
| (e) Sodium Starch Glycollate | 20 | 12 |
| (f) Magnesium Stearate | 5 | 3 |
| | 500 | 300 |

| | mg/tablet |
|---|---|
| Formulation C | |
| Active Ingredient | 100 |
| Lactose B.P. | 200 |
| Povidone B.P. | 50 |
| Sodium Starch Glycollate | 5 |
| Magnesium Stearate | 4 |
| | 359 |

Tablets are prepared from the foregoing ingredients (C) by wet granulation followed by compression. In an alternative preparation the Povidone B.P. may be replaced by Polyvinylpyrrolidone.

The following formulations, D and E, are prepared by direct compression of the admixed ingredients. The lactose in formulation E is of the direct compression type (Dairy Crest-"Zeparox").

| | mg/capsule |
|---|---|
| Formulation D | |
| Active Ingredient | 250 |
| Pregelatinized Starch NF15 | 150 |
| | 400 |
| Formulation E | |
| Active Ingredient | 250 |
| Lactose | 150 |
| Avicel | 100 |
| | 500 |

Formulation F (Controlled Release Formulation)

The formulation is prepared by wet granulation of the ingredients (below) with a solution of povidone followed by the addition of magnesium stearate and compression.

| | | mg/tablet |
|---|---|---|
| (a) | Active Ingredient | 500 |
| (b) | Hydroxypropylmethylcellulose (Methocel K4M Premium) | 112 |
| (c) | Lactose B.P. | 53 |
| (d) | Povidone B.P. | 28 |
| (e) | Magnesium Stearate | 7 |
| | | 700 |

Drug release takes place over a period of about 6–8 hours and is complete after 12 hours.

EXAMPLE 12: Capsule Formulations

Formulation A

A capsule formulation is prepared by admixing the ingredients of Formulation D in Example 12 above and filling into a two-part hard gelatin capsule. Formulation B (infra) is prepared in a similar manner.

| | mg/capsule |
|---|---|
| Formulation B | |
| (a) Active ingredient | 250 |
| (b) Lactose B.P. | 143 |
| (c) Sodium Starch Glycollate | 25 |
| (d) Magnesium Stearate | 2 |
| | 420 |
| Formulation C | |
| (a) Active ingredient | 250 |
| (b) Macrogol 4000 B.P. | 350 |
| | 600 |

Capsules are prepared by melting the Macrogol 4000 BP, dispersing the active ingredient in the melt and filling the melt into a two-part hard gelatin capsule.

| | mg/capsule |
|---|---|
| Formulation D | |
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronization of the extrudate and drying. The dried pellets are then coated with release-controlling membrane (d) and filled into a two-piece, hard gelatin capsule.

| | mg/capsule |
|---|---|
| (a) Active Ingredient | 250 |
| (b) Microcrystalline Cellulose | 125 |
| (c) Lactose B.P. | 125 |
| (d) Ethyl Cellulose | 13 |
| | 513 |

EXAMPLE 13: Ophthalmic Solution

| | | |
|---|---|---|
| Active Ingredient | 0.5 | |
| Sodium chloride, analytical grade | 0.9 | g |
| Thiomersal | 0.001 | g |
| Purified water to | 100 | mL |
| pH adjusted to | 7.5 | |

EXAMPLE 14: Injectable Formulation

| | | |
|---|---|---|
| Active Ingredient | 0.200 | g |
| Sterile, pyrogen free phosphate buffer (pH 7.2) to | 10 | mL |

The active ingredient is dissolved in most of the phosphate buffer (35°–40° C.), then made up to volume and filtered through a sterile micropore filter into a sterile 10 mL amber glass vial (type 1) and sealed with sterile closures and overseals.

EXAMPLE 15: Intramuscular Injection

| Active Ingredient | 0.20 g |
|---|---|
| Benzyl Alcohol | 0.10 g |
| Glycofurol 75 | 1.45 g |
| Water for Injection | q.s. to 3.00 mL |

The active ingredient is dissolved in the glycofurol. The benzyl alcohol is then added and dissolved, and water added to 3 mL. The mixture is then filtered through a sterile micropore filter and sealed in sterile 3 mL amber glass vials (type 1).

EXAMPLE 16: Syrup Suspension

| Active Ingredient | 0.25 g |
|---|---|
| Sorbitol Solution | 1.50 g |
| Glycerol | 2.00 g |
| Dispersible Cellulose | 0.075 g |
| Sodium Benzoate | 0.005 g |
| Flavor, Peach 17.42.3169 | 0.0125 mL |
| Purified Water | q.s. to 5.00 mL |

*The active ingredient is used as a powder wherein at least 90% of the particles are of 63 μM diameter or less.

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

EXAMPLE 17: Suppository

|  | mg/suppository |
|---|---|
| Active ingredient (63 μM)* | 250 |
| Hard Fat, BP (Witepsol H15 - Dynamit Nobel) | 1700 |
|  | 1950 |

One-fifth of the Witepsol H15 is melted in a steam-jacketed pan at 45° C. maximum. The active ingredient is sifted through a 200 μM sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μM stainless steel screen and, with continuous stirring, is allowed to cool to 40° C. At a temperature of 38° C. to 40° C., 2.02 g of the mixture is filled into suitable plastic molds. The suppositories are allowed to cool to room temperature.

EXAMPLE 18: Pessaries

|  | mg/pessary |
|---|---|
| Active ingredient (63 μM)* | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

EXAMPLE 19: Determination of Anti-Varicella-Zoster Virus Activity

The inhibitory effects of compounds on the replication of VZV (Oka strain) were assessed by an ELISA procedure (Berkowitz, F. E., and Levin, M. J. (1985) *Antimicrob. Agents and Chemother.* 28, 207–210)that was modified as follows. Infections were initiated in the presence of drug, rather than before drug addition. At the end of the three-day incubation of drug and virus with uninfected cells (human diploid fibroblasts, strain MRC-5), the 96-well plates were centrifuged for 5 minutes at 200×g to sediment detached cells prior to glutaraldehyde fixation. The present ELISA used an alkaline phosphatase-conjugated anti-human IgG as the second antibody. The rate of cleavage of p-nitrophenyl phosphate by bound alkaline phosphatase was determined as described elsewhere (Tadepalli, S. N., Quinn, R. P., and Averett, D. R. (1986) *Antimicrob. Agents and Chemother.* 29, 93–98). Uninfected cells were used to obtain the blank reaction rates, which were subtracted from the rates obtained with the virus present. This assay was suitable to detect progeny virus in cultures that were initially infected with 15 to 3600 infectious particles per cell.

The anti-varicella zoster virus activity of the compound of Example 9 is 14 μM.

We claim:

1. 2-Amino-6-methoxy-9-(5-O-propionyl-β-D-arabinofuranosyl-9 H-purine.

2. 2-Amino-6-methoxy-9-(5-O-butyryl-β-D-arabinofuranosyl-9 H-purine.

* * * * *

UNITED STATES PATENT AND TRADEMARK OFFICE
CERTIFICATE OF CORRECTION

PATENT NO.  :   5,539,098
DATED       :   July 23, 1996
INVENTOR(S) :   Krenitsky et al.

It is certified that error appears in the above-identified patent and that said Letters Patent is hereby corrected as shown below:

Column 1, after Assignee, please insert the following terminal disclaimer: --The portion of the term of this patent subsequent to June 13, 2012 has been disclaimed.--

Signed and Sealed this

Seventeenth Day of December, 1996

Attest:

BRUCE LEHMAN

Attesting Officer

Commissioner of Patents and Trademarks